United States Patent [19]

Green

[11] Patent Number: 4,617,281

[45] Date of Patent: Oct. 14, 1986

[54] CATALYSIS USING SUPPORTED STRONG BASE CATALYSTS

[75] Inventor: Michael J. Green, Hedon, England

[73] Assignee: BP Chemicals Limited, London, England

[21] Appl. No.: 740,979

[22] Filed: Jun. 4, 1985

[30] Foreign Application Priority Data

Jun. 9, 1984 [GB] United Kingdom ............... 8414767

[51] Int. Cl.$^4$ ..................... B01J 31/06; B01J 31/02
[52] U.S. Cl. ..................................... 502/62; 502/159; 502/167; 502/162; 560/231; 560/234; 568/876; 564/467
[58] Field of Search ................ 502/62, 159, 167, 162

[56] References Cited

U.S. PATENT DOCUMENTS

| | | | |
|---|---|---|---|
| 2,742,515 | 4/1956 | Stuart | 502/167 X |
| 3,274,243 | 9/1966 | Gilbert et al. | 502/167 X |
| 3,594,358 | 7/1971 | Moberly | 502/159 X |
| 3,625,755 | 12/1971 | Potrafke | 502/159 X |
| 3,708,462 | 1/1973 | McKinley et al. | 502/159 X |
| 3,839,065 | 10/1974 | Overholts et al. | 502/167 X |
| 3,997,472 | 12/1976 | O'Driscoll et al. | 502/159 |
| 4,059,542 | 11/1977 | Jennings et al. | 502/167 X |
| 4,290,917 | 9/1981 | Carlson | 502/167 X |
| 4,327,225 | 4/1982 | Isogai et al. | 502/167 X |
| 4,519,954 | 5/1985 | Burrington et al. | 502/167 X |

OTHER PUBLICATIONS

Rideal, *Concepts in Catalysis,* published by Academic Press, London & New York (1968), p. 5.

*Primary Examiner*—Patrick P. Garvin
*Attorney, Agent, or Firm*—Brooks Haidt Haffner & Delahunty

[57] ABSTRACT

A catalyst suitable for use in reactions catalyzed by strong base is provided. The catalyst comprises an organic compound containing a Group VA element for example an amine or phosphine supported on a solid which is insoluble in the reaction mixture. The catalyst may be activated by treatment with an epoxide. Catalysts in which the amine is an amidine or a guanidine are particularly effective.

17 Claims, No Drawings

CATALYSIS USING SUPPORTED STRONG BASE CATALYSTS

The present invention relates to novel catalysts and the uses thereof.

It is known that transition metal complex catalysts which are generally used in solution for liquid phase catalysis can be supported or chemically bonded to an insoluble inert solid. Such supported catalysts have the advantage that, particularly in a continuously operated liquid-phase process, the catalyst is essentially immobilised thereby avoiding problems associated with catalyst recovery.

It has now been found that strong bases for example amidines and guanidines, can be supported on an insoluble solid and used as catalysts for a number of base catalysed reactions. Such catalysts have the advantages that they are easy to manipulate, store and transport and are easily separated from any liquid medium in which a reaction is carried out thereby obviating the need for expensive, energy intensive recovery processes such as distillation.

Accordingly, the present invention provides catalyst for use in reactions catalysed by strong base, the catalyst being insoluble in the reaction mixture, characterised in that the catalyst comprises an organic compound containing a Group VA element supported on an insoluble solid selected from an organic resin, an organic polymer or an inorganic oxide.

The catalysts of the present invention are particularly suitable for use in three types of reaction (a) the production of formate esters or formamides by the carbonylation of an alcohol or an amine, (b) the production of an alcohol by decarbonylation of an alkyl formate and (c) the transesterification of carboxylic or carbonic acid esters.

Accordingly in a first embodiment of the invention there is provided a process for the production of a formamide by the carbonylation of an alcohol or an amine which process comprises reacting the alcohol or ammonia or an amine with carbon monoxide at elevated temperature characterised in that the reaction is carried out in the presence of a catalyst of the type described above.

In a second embodiment, there is provided a process for the production of an alcohol from an alkyl formate by decarbonylation which comprises reacting the alkyl formate at elevated temperature with a catalyst characterised in that a catalyst of the type described above is used.

In a third embodiment, there is provided a process for the transesterification of carboxylic or carbonic acid esters by reacting the ester with an alcohol in the presence of an effective amount of a catalyst characterised in that a catalyst as described above is used.

As regards the organic compound containing a Group VA element, this is suitably an amine or a phosphine. A preferable class of amines are the amidines and guanidines.

By the term amidine is meant a compound containing the grouping

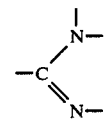

Conveniently the free valencies on the nitrogen atom are attached to carbon atoms or hydrogen and the free valency on the carbon to another carbon or nitrogen atoms. In the last mentioned case the structure will comprise a guanidine grouping.

A preferred class of amidines is the cyclic amidines. Cyclic amidines are defined as those amidines wherein at least one of the nitrogen atoms is part of an alicyclic or heterocyclic substituted or unsubstituted hydrocarbyl ring. In the case where the amidine is a guanidine then any two of the three nitrogen atoms may be in the same or different rings. Those nitrogen atoms which are not part of any said ring may form part of a substituted or unsubstituted hydrocarbyl group.

A preferred class of cyclic amidine is that in which the amidine group can form part of a fused ring system containing 6 and 5 membered rings or 6 and 7 membered rings or two six membered rings, as for example in 1,5-diazabicyclo[4.3.0]non-5-ene (DBN), or 1,8-diazabicyclo[5.4.0]undec-7-ene (DBU) or 1,5,7-triazabicyclo[4.4.0]dec-5-ene (TBD).

The amidine or guandine is supported, that is chemically and physically bonded, or incorporated into the insoluble solid. This is achieved by bonding the surface atoms of the solid to one or more of the free valences of the amidine or guanidine group either directly or through an intermediate hydrocarbyl radical. In the case of cyclic amidines or guanidines the hydrocarbyl radical may constitute part of the ring structure of the molecule.

A second preferred class of organic compound containing a Group VA element is that comprising mono-, di- and trialkylamines and alkylphosphines, arylamines an arylphosphines. When these are used as the organic compound containing a Group VA element it is preferable to use the catalyst in combination with an epoxide. This can be done by (a) activating the catalyst prior to use by refluxing it with the epoxide, (b) adding the catalyst and the epoxide separately to the appropriate reaction mixture thereby allowing the activation to occur in situ or (c) chemically binding the epoxide to the insoluble solid prior to supporting the organic compound containing a Group VA element.

The amine or phosphine is preferably bonded to the insoluble solid through one or more of the hydrocarbyl groups appendant to the nitrogen or phosphorus atom. Preferred examples of amines or phosphines which can be supported in the insoluble solid are derivatives or trimethylamine, trimethylphosphine, tributylamine, tributylphosphine and the like wherein one or more of the hydrocarbyl groups have been modified in a way such that they are bondable to the surface of the solid.

The epoxide used in conjunction with the supported amine or phosphine is conveniently a lower alkylene oxide, for example ethylene oxide, propylene oxide and butylene oxide.

The insoluble solid is selected from an organic resin, an organic polymer or an inorganic oxide. If the support is an organic polymer, it is preferably polystyrene, a polystyrene/divinylbenzene copolymer or polyvinylpyridine. In the case of polyvinylpyridine and similar polymers where the Group VA element is at least in part incorporated into the polymer backbone, it will be appreciated by the skilled man that since this is a polymer which already contains a Group VA element such materials can be used as catalyst without further modification other than epoxide activation.

If the insoluble solid is an inorganic oxide, it is preferably selected from a silica, an alumina, a clay, a diatomaceous earth, a zeolite or an aluminosilicate. When such inorganic oxides are used, it is preferable, after the catalyst has been prepared, to remove any residual hydroxyl groups on the inorganic oxide using a chemical such as hexamethyldisilanzane.

Examples of the catalyst which can be used are TBD supported on polystyrene or polystyrene/divinylbenzene copolymer, Amberlite IRA-93, Amberlyst 15 and Duolite A375, tetramethylguanidine on silica, imidazole on silica and the like.

The organic compound containing a Group VA element is preferably present on the solid in amounts corresponding to between 0.1 to 10 moles per gram of solid.

It is clearly important that the solid is not degraded under the conditions of the particular application for which it is used. Hence by the term "insoluble solid" is meant a solid which does not undergo substantial physical or chemical degradation under the conditions of the particular application. Since the conditions vary from reaction to reaction the exact nature of the solid will depend on the desired application of the catalyst.

In use, the catalyst described above are suitably added to the appropriate reaction mixture in amounts corresponding to between 0.1 and 50% by weight of the total.

As mentioned earlier, the catalysts described above are particularly suitable for three types of reaction. The conditions under which these reactions are carried out, together with the range of feedstocks which can be used are described in our European patent application Nos. 104875, 115387 and 110629.

The invention is now described with reference to the following Examples.

EXAMPLE 1

Preparation of a tetramethylguanidine on silica

Silica gel (9 g), 2-[3-(triethoxysilyl)-propyl]-1,1,3,3-tetramethylguanidine (9 g) and 50 mls of toluene were added to a 100 ml round bottom flask under an atmosphere of dry nitrogen gas. The mixture was then heated and refluxed for 4 hours. At the end of this time the contents of the flask were cooled and the catalyst separated from the liquid components by filtration and washed with 100 ml of methanol.

EXAMPLE 2

0.3 g of the catalyst produced in Example 1 was transferred to a 100 ml conical flask together with 10 g of methanol and 10 g of ethyl acetate. The resulting mixture was stirred at room temperature and liquid samples removed periodically for analysis by gas chromatography.

| Time | % Conversion of ethyl acetate to methyl acetate |
| --- | --- |
| 15 min | 7 |
| 45 min | 21 |
| 75 min | 30 |
| 105 min | 40.5 |
| 19 hours | 69 |

The 15 min sample was re-analysed after 19 hours; the composition of the solution remained unchanged. The composition of the solution remained unchanged which shows that (1) the catalysed is insoluble and (2) no reaction occurs in the absence of catalyst.

EXAMPLE 3

Preparation of tetramethylguanidine on alumina

The procedure of Example 1 was used except that 9 g of alumina was used in place of 9 g of silica. The catalyst produced after 4 hours reflux was filtered and washed with 100 ml of toluene.

EXAMPLE 4

The catalyst of Example 3 was used under the conditions of Example 2 except that 0.4 g of catalyst was used. Analysis of the liquid product after 19 hours showed a 27% conversion of ethyl acetate to methyl acetate.

EXAMPLE 5

Example 4 was repeated except that the catalyst was activated by treatment with 0.5 g of butene oxide in refluxing methanol prior to the addition of ethyl acetate. Analysis of the liquid product after 19 hours showed a 35% conversion of ethyl to methyl acetate.

EXAMPLE 6

3 g of silica supported imidazole (2% nitrogen content) 10 ml of 1,1,1,3,3,3-hexamethyldisilazane and 50 mls of toluene were charged to a 100 ml round bottomed flask and refluxed gently for 1 hour. On cooling, the silica was filtered and washed with 40 ml of toluene followed by 100 ml of methanol. The resulting resin was activated with butene oxide (0.5 g) by refluxing the mixture in methanol (10 g) at atmospheric pressure (1 hour). On cooling, 10 g of ethyl acetate was added and the resulting mixture stirred at room temperature. Analysis of the liquid product after 24 hours showed a 27% conversion of ethyl to methyl acetate.

EXAMPLE 7

0.5 g of a resin composed of 60% poly(4-vinyl) pyridine and 40% 2,4-divinyl-6-methyl pyridine was refluxed with 0.5 g of butene oxide and 10 g of methanol for 1 hour. On cooling, 10 g of ethyl acetate was added, and the resulting mixture stirred at room temperature. Liquid samples were removed periodically for analysis by gas chromatography.

| Time | % Conversion of methyl acetate to ethyl acetate |
| --- | --- |
| 15 min | 11 |
| 45 min | 27 |
| 75 min | 39 |
| 105 min | 47.5 |
| 18 hours | 74 |

The 15 min sample was re-analysed after 24 hours. The composition of the solution remained unchanged.

EXAMPLE 8

150 ml of dry methanol was passed through a fixed bed consisting of 10 g of Duolite A375 resin, for a period of 1 hour. The resulting resin, 15 g of methanol, and 1 g of propylene oxide were heated to 80° C. in a sealed Fischer-Porter tube under an initial nitrogen pressure of 50 psi. After 1 hour, the contents of the tube were cooled and transferred to a 100 ml conical flask together with 30 g of ethyl acetate. The resulting mixture was stirred at room temperature and liquid samples removed periodically for analysis by gas chromatography.

| Time | % Conversion of ethyl acetate to methyl acetate |
|---|---|
| 15 min | 26 |
| 30 min | 46 |
| 45 min | 60 |
| 60 min | 69 |
| 24 hours | 82 |

The 15 min sample was re-analysed after 24 hours.

EXAMPLE 9

100 ml of dry methanol was passed through a fixed bed consisting of 2 g of Duolite A375, for a period of 1 hour. The resulting resin, 10 g of methanol, and 0.4 g of propylene oxide were heated to 80° C. in a sealed Fischer Porter tube under an initial nitrogen pressure of 50 psi. After 1 hour, the contents of the tube were cooled and transferred to a 100 ml conical flask together with 10 g ethyl acetate. The resulting mixture was stirred at room temperature and liquid samples removed periodically for analysis by gas chromatography.

| Time (mins) | % Conversion of ethyl acetate to methyl acetate |
|---|---|
| 15 | 24 |
| 30 | 40 |
| 60 | 62 |
| 90 | 70 |
| 105 | 72 |

EXAMPLE 10

Example 9 was repeated except that 0.5 g of butylene oxide was used in place of propylene oxide.

| Time (mins) | % Conversion of ethyl acetate to methyl acetate |
|---|---|
| 15 | 21 |
| 45 | 53 |
| 60 | 60 |
| 95 | 71 |
| 130 | 76 |

EXAMPLE 11

Example 9 was repeated except that the resin was activated with butylene oxide by refluxing the mixture in methanol at atmospheric pressure.

| Time (mins) | % Conversion of ethyl acetate to methyl acetate |
|---|---|
| 15 | 22 |
| 30 | 40.5 |
| 45 | 52 |
| 60 | 63 |
| 85 | 74 |
| 105 | 78 |

EXAMPLE 12

Example 11 was repeated in the presence of 1 g of butylene oxide. Analysis of the liquid product after 1 hour showed an ethyl acetate conversion of 64% to methyl acetate.

EXAMPLE 13

Example 11 was repeated in the presence of 0.25 g of butylene oxide. Analysis of the liquid product after 1 hour showed an ethyl acetate conversion of 49% to methyl acetate.

EXAMPLE 14

Example 11 was repeated except that 0.92 g of Amberlyst 15 was used in place of Duolite A375. Analysis of the liquid product after 90 min showed a 34% conversion of ethyl acetate to methyl acetate.

EXAMPLE 15

Example 11 was repeated except that 1.05 g of Amberlite IRA93 was used in place of Duolite A375. Analysis of the liquid product after 90 min showed a 19% of ethyl acetate to methyl acetate.

EXAMPLE 16

Example 11 was repeated except that 10 g of propylene carbonate was used in place of ethyl acetate. Analysis of the liquid product after 1 hour showed a propylene carbonate conversion of 28% to dimethyl carbonate.

EXAMPLE 17

Ethyl acetate (10 g) was added to a stirred mixture consisting of 10 g of methanol and 1.4 g of polystyrene supported 1,5,7-triazabicyclo(4.4.0)dec-5-ene (polymer supported TBD). Analysis of the liquid product after 45 min showed an ethyl acetate conversion of 75% to methyl acetate.

EXAMPLE 18

Example 17 was repeated in the presence of 0.5 g of polymer supported TBD. Analysis of the liquid product showed a 63% conversion of ethyl to methyl acetate.

EXAMPLE 19

A 50 ml high pressure stirred autoclave was charged with 7 g of methanol, 5 g of diethylamine and 2 g of polymer supported TBD. The autoclave was sealed and flushed twice with carbon monoxide, following which it was pressurised to 95 bar with carbon monoxide and heated to 120° C. with stirring. After 2 hours the autoclave was cooled to room temperature. Analysis of the liquid product showed a 52% conversion of diethylamine to diethyl formamide.

EXAMPLE 20

The autoclave used in Example 19 was charged with 10 g of n-butyl formate and 2 g for polymer supported TBD. The autoclave was sealed, flushed twice with nitrogen, following which it was pressurised to 25 bar with nitrogen and heated to 150° C. with stirring. The pressure in the autoclave increased to 40 bar. After 2 hours the autoclave was cooled to room temperature. Analysis of the liquid product showed an n-butyl formate conversion of 40% with a quantitative yield of n-butanol and carbon monoxide.

EXAMPLE 21

The autoclave described in Example 19 was charged with 15 g of methanol and 2 g of polymer supported TBD. The autoclave was sealed, flushed twice with carbon monoxide and pressurised to 100 bar with carbon monoxide. The autoclave was heated to 120° C. and maintained at this temperature for 2 hours. Analysis of the cooled liquid product showed a 14% conversion of methanol to methyl formate.

I claim:

1. A catalyst composition suitable for use in reactions catalysed by a strong base, which catalyst comprises a reaction media insoluble amine or phosphine supported on a reaction media insoluble organic polymer or an inorganic oxide solid, said catalyst having been activated with an alkylene epoxide.

2. A catalyst as claimed in claim 1 characterised in that the amine is an amidine or guanidine.

3. A catalyst as claimed in claim 2 characterised in that the amidine or guanidine is a cyclic amidine or guanidine.

4. A catalyst as claimed in claim 1 characterised in that the organic polymer is polystyrene, polystyrene/divinylbenzene copolymer or polyvinylpyridine.

5. A catalyst as claimed in claim 1 characterised in that the inorganic oxide is selected from silica, alumina, a clay, a diatomaceous earth, a zeolite and an aluminosilicate.

6. A catalyst as claimed in claim 5 characterised in that the residual surface hydroxyl groups of the inorganic oxide are romoved before the catalyst is used.

7. A catalyst as claimed in claim 1, wherein the amine is a trialkylamine.

8. A catalyst as claimed in claim 2, wherein the amidine is 1,5-diazabicyclo[4.3.0]non-5-ene or 1,8-diazabicyclo[5.4.0]undec-7-ene.

9. A catalyst as claimed in claim 2, wherein the guanidine is 1,5,7-triazabicyclo[4.4.0]dec-5-ene.

10. A catalyst as claimed in claim 1, wherein the phosphine is a trialkyl phosphine.

11. A catalyst as claimed in claim 1, wherein the epoxide is a lower alkylene oxide.

12. A catalyst as claimed in claim 1, wherein the epoxide is selected from the group consisting of ethylene oxide, propylene oxide and butylene oxide.

13. A process for preparing a catalyst composition suitable for use in strong base catalysed reactions, which comprises treating a catalyst comprising a reaction media insoluble amine or phosphine and a reaction media insoluble inorganic metal oxide or organic polymer solid with an alkylene epoxide.

14. A process as defined in claim 13 in which the alkylene epoxide is brought into contact with the catalyst prior to use.

15. A process for preparing the catalyst of claim 13, comprising activating the catalyst prior to use by refluxing the catalyst with the epoxide.

16. A process for preparing the catalyst of claim 13, comprising adding the catalyst and the epoxide separately to the appropriate reaction mixture thereby allowing the activation to occur in situ.

17. A process for preparing the catalyst of claim 13, comprising chemically binding the epoxide to the insoluble solid prior to supporting the amine or phosphine.

* * * * *

UNITED STATES PATENT AND TRADEMARK OFFICE
CERTIFICATE OF CORRECTION

PATENT NO. : 4,617,281

DATED : October 14, 1986

INVENTOR(S) : Michael James Green

It is certified that error appears in the above-identified patent and that said Letters Patent is hereby corrected as shown below:

Col. 5, line 32 after "10 g" and before "ethyl" insert --of--

Col. 6, line 67, change "for" to --of--

Claim 6. line 3, correct spelling of "removed"

Signed and Sealed this

First Day of September, 1987

Attest:

DONALD J. QUIGG

*Attesting Officer*   *Commissioner of Patents and Trademarks*